US009457012B2

(12) United States Patent
Watanabe et al.

(10) Patent No.: US 9,457,012 B2

(45) Date of Patent: Oct. 4, 2016

(54) TRANSDERMAL ABSORPTION PREPARATION

(71) Applicants: KYORIN PHARMACEUTICAL CO., LTD., Tokyo (JP); TEIKOKU SEIYAKU CO., LTD., Kagawa (JP)

(72) Inventors: Masato Watanabe, Tochigi (JP); Norihiro Kanayama, Tochigi (JP)

(73) Assignee: TEIKOKU SEIYAKU CO., LTD., Kagawa (JP)

( * ) Notice: Subject to any disclaimer, the term of this patent is extended or adjusted under 35 U.S.C. 154(b) by 0 days.

(21) Appl. No.: 14/384,267

(22) PCT Filed: Mar. 21, 2013

(86) PCT No.: PCT/JP2013/001902

§ 371 (c)(1),
(2) Date: Sep. 10, 2014

(87) PCT Pub. No.: WO2013/140799

PCT Pub. Date: Sep. 26, 2013

(65) Prior Publication Data

US 2015/0064232 A1 Mar. 5, 2015

(30) Foreign Application Priority Data

Mar. 22, 2012 (JP) ................................ 2012-065344

(51) Int. Cl.

| | |
|---|---|
| ***A61K 9/72*** | (2006.01) |
| ***A61K 31/4174*** | (2006.01) |
| ***A61K 9/00*** | (2006.01) |
| ***A61K 9/70*** | (2006.01) |
| ***A61K 47/12*** | (2006.01) |
| ***A61K 47/14*** | (2006.01) |

(52) U.S. Cl.

CPC ......... *A61K 31/4174* (2013.01); *A61K 9/0014* (2013.01); *A61K 9/7023* (2013.01); *A61K 9/7038* (2013.01); *A61K 9/7053* (2013.01); *A61K 9/7084* (2013.01); *A61K 47/12* (2013.01); *A61K 47/14* (2013.01)

(58) Field of Classification Search

CPC ............. A61K 9/7023; A61K 9/7053; A61K 9/7084; A61L 9/7038

See application file for complete search history.

(56) References Cited

FOREIGN PATENT DOCUMENTS

| | | |
|---|---|---|
| WO | 96/15793 | 5/1996 |
| WO | 00/61120 | 10/2000 |
| WO | 2005/011683 | 2/2005 |
| WO | 2006/082888 | 8/2006 |
| WO | 2006/118173 | 11/2006 |

OTHER PUBLICATIONS

International Search Report issued May 14, 2013 in International (PCT) Application No. PCT/JP2013/001902.
Abstract of JP 5-43457, Feb. 23, 1993.
International Preliminary Report on Patentability issued Sep. 23, 2014 in International (PCT) Application No. PCT/JP2013/001902.

*Primary Examiner* — Carlos Azpuru

(74) *Attorney, Agent, or Firm* — Wenderoth, Lind & Ponack, L.L.P.

(57) ABSTRACT

A transdermal absorption preparation comprising (1) a support, and (2) a rubber-based adhesive layer comprising 4-(2-methyl-1-imidazolyl)-2,2-diphenylbutylamide or a pharmaceutically acceptable salt thereof, oleic acid, capric acid and crotamiton, wherein the rubber-based adhesive layer is formed on a surface of the support. The transdermal absorption preparation exhibits excellent transdermal absorption of the 4-(2-methyl-1-imidazolyl)-2,2-diphenylbutylamide or salt thereof.

9 Claims, 2 Drawing Sheets

FIG. 1

| COMPONENT | AMOUNT (w/w%) | | | | | | | | | | | | | | | |
|---|---|---|---|---|---|---|---|---|---|---|---|---|---|---|---|---|
| | EXAMPLE | | COMPARATIVE EXAMPLE | | | | | | | | | | | | | |
| | 1 | 2 | 1 | 2 | 3 | 4 | 5 | 6 | 7 | 8 | 9 | 10 | 11 | 12 | 13 | 14 |
| STYRENE—ISOPRENE—STYRENE BLOCK COPOLYMER | 37.1 | 37.1 | 37.1 | 37.1 | 39.1 | 37.6 | 39.1 | 39.0 | 40.0 | 37.6 | 37.1 | 39.1 | 38.1 | 39.1 | 40.0 | 40.5 |
| HYDROGENATED ROSIN GLYCEROL ESTER | 40.0 | 41.0 | 41.0 | 40.9 | 43.0 | 41.4 | 44.0 | 44.0 | 44.0 | 41.5 | 41.9 | 44.0 | 41.9 | 45 | 44.0 | 44.5 |
| ISOPROPYL MYRISTATE | 10 | | | | | | | | | | | | | | | |
| OLEIC ACID | 5 | | 5 | 5 | - | 5 | - | - | - | 5 | 5 | - | 5 | - | - | - |
| CAPRIC ACID | 0.9 | | 0.9 | - | 0.9 | - | 0.9 | - | - | 0.9 | - | 0.9 | - | 0.9 | - | - |
| CROTAMITON | 1 | | - | 1 | 1 | - | - | 1 | - | - | 1 | 1 | - | - | 1 | - |
| LACTIC ACID | 1 | - | 1 | | | | | | | - | | | | | | |
| IMIDAFENACIN | 5 | | | | | | | | | | | | | | | |

TRANSDERMAL ABSORPTION PREPARATION

TECHNICAL FIELD

The present invention relates to a transdermal absorption preparation containing 4-(2-methyl-1-imidazolyl)-2,2-diphenylbutylamide or a pharmaceutically acceptable salt thereof as an active ingredient.

BACKGROUND ART 4-(2-methyl-1-imidazolyl)-2,2-diphenylbutylamide (imidafenacin) is a compound having a selective M1/M3 muscarine receptor antagonistic action, and for example is known as a therapeutic agent for pollakiuria and urinary incontinence accompanying overactive bladder.

As the dosage form of imidafenacin, a transdermal absorption preparation has been proposed in addition to a solid oral preparation (for example, Patent Documents 1 and 2). In the transdermal absorption preparation, for example, imidafenacin is easily administered even to the elderly and the like. Further, a temporary increase in the blood level, which may be caused in oral administration, can be suppressed.

CITATION LIST

Patent Documents

Patent Document 1: WO2005/011683 Pamphlet
Patent Document 2: WO2006/082888

SUMMARY OF THE INVENTION

Problems to be Solved by the Invention

In general, the absorbability of a drug in transdermal administration is lower than that in oral administration due to a barrier function of the skin for preventing any foreign material from entering the body. In a transdermal absorption preparation, it is difficult in many cases to secure a blood level necessary for development of beneficial effects. Therefore, a drug that is capable of administration in the form of the transdermal absorption preparation is restricted. Since the absorbability of imidafenacin through the skin is very low, improvement of transdermal absorbability is required in administration of imidafenacin as the transdermal absorption preparation.

The present invention has been made on the basis of such circumstances and it is an object of the present invention to provide a transdermal absorption preparation exhibiting excellent transdermal absorbability for 4-(2-methyl-1-imidazolyl)-2,2-diphenylbutylamide or a pharmaceutically acceptable salt thereof.

Means to Solve the Problems

For examples, aspects of the present invention are as follows.

1) A transdermal absorption preparation having a support and a rubber-based adhesive layer that is formed on the surface of the support and contains 4-(2-methyl-1-imidazolyl)-2,2-diphenylbutylamide or a pharmaceutically acceptable salt thereof, wherein the rubber-based adhesive layer further contains oleic acid, capric acid, and crotamiton.

2) The transdermal absorption preparation according to 1), wherein the rubber-based adhesive layer further contains a carboxylic acid having 2 to 10 carbon atoms.

3) The transdermal absorption preparation according to 2), wherein the carboxylic acid having 2 to 10 carbon atoms is lactic acid.

4) The transdermal absorption preparation according to any one of 1) to 3), wherein the rubber-based adhesive layer further contains a fatty acid ester having 6 to 20 carbon atoms.

5) The transdermal absorption preparation according to 4), wherein the fatty acid ester having 6 to 20 carbon atoms is isopropyl myristate.

Another aspect of the present invention relates to a composition that contains a rubber-based adhesive, oleic acid, capric acid, and crotamiton, and enhances transdermal absorption of 4-(2-methyl-1-imidazolyl)-2,2-diphenylbutylamide or a pharmaceutically acceptable salt thereof. The composition can be used, for example, as a composition constructing an adhesive layer of a transdermal absorption preparation.

Advantageous Effects of the Invention

The present invention can provide a transdermal absorption preparation exhibiting excellent transdermal absorbability for 4-(2-methyl-1-imidazolyl)-2,2-diphenylbutylamide or a pharmaceutically acceptable salt thereof.

BRIEF DESCRIPTION OF DRAWINGS

FIG. 1 is a table showing a composition of components that are contained in an adhesive layer of a transdermal absorption preparation in each of Examples and Comparative Examples.

DESCRIPTION OF EMBODIMENTS

Figure 2:
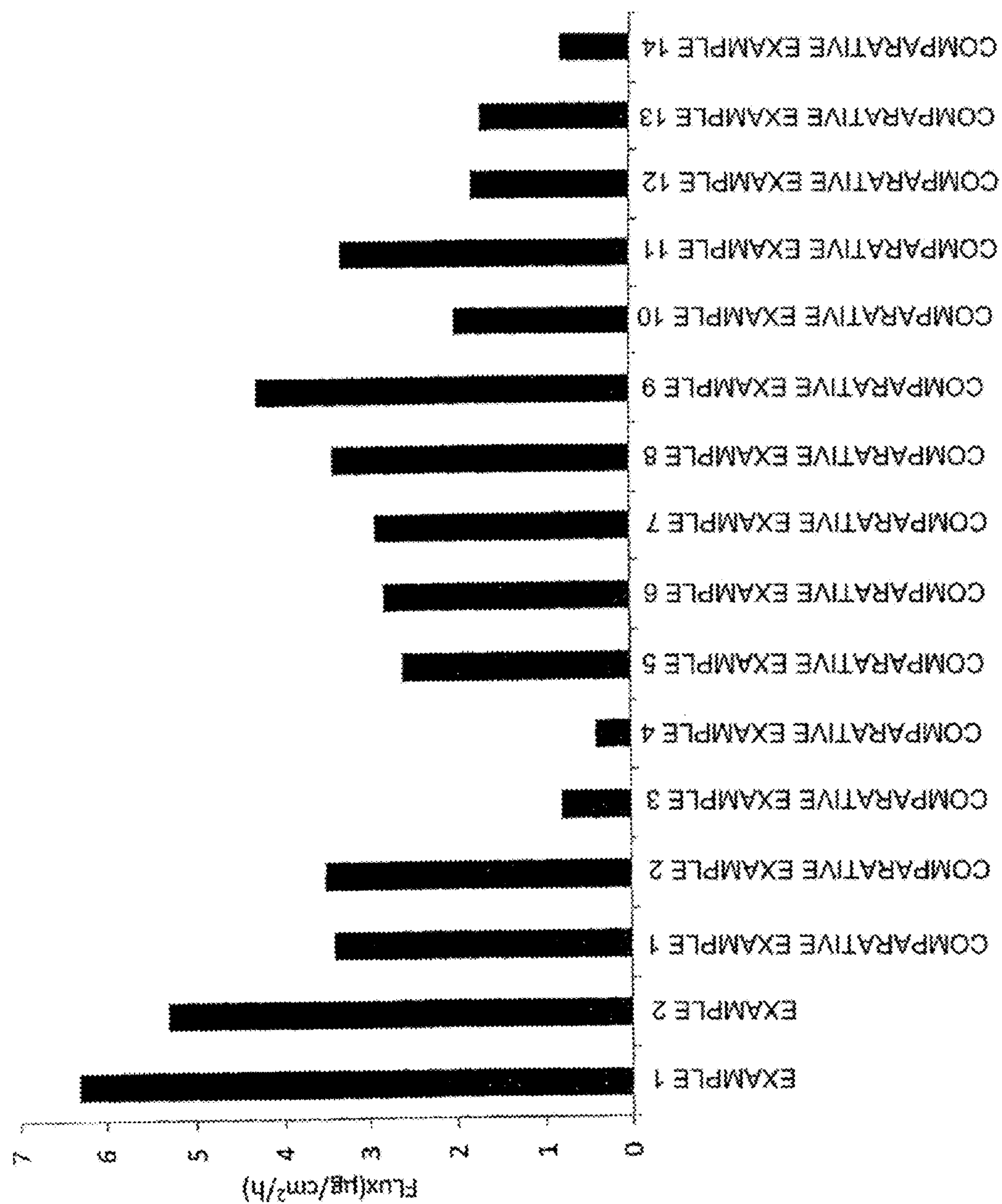
FIG. 2 is a graph showing a FLUX value of the transdermal absorption preparation in each of Examples and Comparative Examples.

Hereinafter, one of embodiments of the present invention will be described in detail.

A transdermal absorption preparation of this embodiment has a support and a rubber-based adhesive layer (hereinafter sometimes simply referred to as adhesive layer) that is formed on the surface of the support and contains a rubber-based adhesive. The adhesive layer contains 4-(2-methyl-1-imidazolyl)-2,2-diphenylbutylamide or a pharmaceutically acceptable salt thereof as an active ingredient.

In order to facilitate understanding, free 4-(2-methyl-1-imidazolyl)-2,2-diphenylbutylamide and a pharmaceutically acceptable salt thereof in the following description are collectively referred to as imidafenacin.

A transdermal absorption preparation herein means a dosage form of a pharmaceutical that allows a drug to to be absorbed in the body through the skin by applying the preparation to the skin. For example, a drug introduced into the body through the skin is absorbed in the capillaries and delivered to a site of action along the flow of blood.

Herein, components contained in the rubber-based adhesive layer other than the rubber-based adhesive and imidafenacin as an active ingredient are collectively referred to as an additive. The additive includes oleic acid, capric acid, crotamiton, and other components to be contained if necessary (a carboxylic acid having 2 to 10 carbon atoms, a fatty acid ester having 6 to 20 carbon atoms, and/or other components).

Herein, the ratio of each component in the adhesive layer to the total components in the adhesive layer is based on the total mass of the adhesive layer containing the rubber-based adhesive, imidafenacin, and the additive. Provided that the total mass of the adhesive layer that is a standard does not contain the mass of an organic solvent that is sometimes used in production.

The adhesive layer of this embodiment contains a rubber-based adhesive (rubber-based polymer) as the adhesive.

For example, natural rubber or synthetic rubber can be used as the rubber-based adhesive. Examples of synthetic rubber may include polyisobutylene rubber (high molecular weight polyisobutyrene rubber, low molecular weight polyisobutyrene rubber, or a mixture thereof), cis-polyisoprene rubber, high cis-polyisoprene rubber, a styrene-isoprene-based block copolymer such as a styrene-isoprene block copolymer and a styrene-isoprene-styrene block copolymer, and a styrene-butadiene-based block copolymer such as a styrene-butadiene block copolymer, a styrene-butadiene-styrene block copolymer, and a styrene-ethylene-butadiene-styrene block copolymer.

A mixture of some kinds of rubber-based polymers can be also used as the rubber-based adhesive according to this embodiment.

The ratio of the rubber-based adhesive to the total components contained in the adhesive layer is not particularly limited, and for example, can be set to 20 to 60% by mass (preferably 30 to 50% by mass).

The adhesive layer contains imidafenacin as an active ingredient, specifically, 4-(2-methyl-1-imidazolyl)-2,2-diphenylbutylamide or a pharmaceutically acceptable salt thereof.

Imidafenacin may be contained as either a soluble type or a mixture type of a soluble type and an insoluble type. The soluble type means that imidafenacin is completely dissolved in the adhesive layer, and particularly that crystals of imidafenacin in the adhesive layer are not observed by eye or with an optical microscope. On the other hand, the insoluble type means that imidafenacin is present in a crystalline state or an amorphous state in the adhesive layer. A soluble-type imidafenacin is absorbed in the body through the skin. An insoluble-type imidafenacin itself is not absorbed in the body, but is converted into a soluble type as the amount of soluble-type imidafenacin decreases after its transdermal absorption. Specifically, the insoluble-type imidafenacin acts as a source of a soluble-type imidafenacin.

In the transdermal absorption preparation of this embodiment, imidafenacin contained in the adhesive layer is preferably a soluble-type from the viewpoints of rapid transdermal absorbability and quality stability including skin adhesive properties.

Examples of the pharmaceutically acceptable salt of 4-(2-methyl-1-imidazolyl)-2,2-diphenylbutylamide may include inorganic acid salts such as hydrochloride, sulfate, and hydrobromide, and organic acid salts such as maleate, fumarate, acetate, oxalate, tartrate, and benzenesulfonate.

The ratio of imidafenacin to the total components contained in the adhesive layer is not particularly limited, and for example, can be set to 1 to 10% by mass (preferably 1 to 8% by mass, and more preferably 1 to 6% by mass).

In the transdermal absorption preparation of this embodiment, the adhesive layer contains oleic acid, capric acid, and crotamiton. When the adhesive layer contains oleic acid, capric acid, and crotamiton, the transdermal absorbability of imidafenacin can be enhanced.

Oleic acid, for example, acts as an agent for dissolving imidafenacin in a rubber-based adhesive.

Capric acid, for example, acts as a dissolving agent, like oleic acid.

Further, crotamiton, for example, acts as an absorption enhancer of imidafenacin in the body.

The ratios of oleic acid, capric acid, and crotamiton to the total components contained in the adhesive layer are not particularly limited. For example, the ratio of oleic acid to the total components contained in the adhesive layer can be set to 1 to 10% by mass (preferably 3 to 10% by mass). The ratio of capric acid to the total components contained in the adhesive layer can be set to 0.1 to 10% by mass (preferably 0.5 to 10% by mass). The ratio of crotamiton to the total components contained in the adhesive layer can be set to 0.1 to 10% by mass (preferably 1 to 10% by mass).

In the transdermal absorption preparation of this embodiment, it is preferable that in addition to oleic acid, capric acid, and crotamiton, the rubber-based adhesive layer containing imidafenacin further contain a carboxylic acid having 2 to 10 carbon atoms, such as lactic acid. In a more preferable aspect, the rubber-based adhesive layer of the transdermal absorption preparation containing imidafenacin contains a fatty acid ester having 6 to 20 carbon atoms such as isopropyl myristate, as described below, in addition to oleic acid, capric acid, crotamiton, and a carboxylic acid having 2 to 10 carbon atoms.

For example, the carboxylic acid having 2 to 10 carbon atoms acts as the dissolving agent, like oleic acid. Examples of the carboxylic acid having 2 to 10 carbon atoms may include acetic acid, propionic acid, butyric acid, pentanoic acid, and heptanoic acid. As the carboxylic acid having 2 to 10 carbon atoms, hydroxy acid that is a carboxylic acid having an alcoholic or phenolic hydroxyl group can also be used. Examples of hydroxy acid may include lactic acid, tartaric acid, and citric acid. In this embodiment, from the viewpoint of solubility of imidafenacin, hydroxy acid is preferably used, and lactic acid is more preferably used.

The ratio of carboxylic acid having 2 to 10 carbon atoms to the total components contained in the adhesive layer can be set to 0.1 to 10% by mass (preferably 1 to 5% by mass).

In the transdermal absorption preparation of this embodiment, when the adhesive layer contains a fatty acid ester having 6 to 20 carbon atoms, the physical properties of the adhesive layer can be optimized, and the transdermal absorbability of imidafenacin can be further enhanced.

For example, the fatty acid ester having 6 to 20 carbon atoms acts as a softener for enhancing the adhesive properties of the rubber-based adhesive. Examples of the fatty acid ester having 6 to 20 carbon atoms may include isopropyl myristate, isopropyl palmitate, and oleyl oleate. In this embodiment, isopropyl myristate is preferably used.

The ratio of fatty acid ester having 6 to 20 carbon atoms to the total components contained in the adhesive layer can be set to 2 to 20% by mass, and preferably 5 to 15% by mass.

In this embodiment, the adhesive layer may further contain other components as the additive. Examples of the additive may include a tackifying resin.

When the tackifying resin is mixed with the rubber-based polymer in the adhesive layer, examples of the tackifying resin may include rosin, rosin derivatives such as a glycerol ester of rosin, a hydrogenated rosin, a hydrogenated rosin glycerol ester, and a pentaerythritol ester of rosin, an alicyclic saturated hydrocarbon resin, an aliphatic hydrocarbon resin, and a terpene resin.

Specifically, when a styrene-isoprene-styrene block copolymer is used as the rubber-based adhesive, a hydrogenated rosin glycerol ester can be used as the tackifying resin.

When the tackifying resin is mixed with the rubber-based polymer, the ratio of the tackifying resin to the total components contained in the adhesive layer is not particularly limited, and for example, can be set to 20 to 60% by mass (preferably 30 to 50% by mass).

One or two or more of other dissolving agents, other softeners, other absorption enhancers, a skin irritation alleviating agent, and an antioxidant may be contained as the other component exemplified as the additive.

Examples of the dissolving agent may include a higher fatty acid ester (isopropyl palmitate, oleyl oleate, etc.), a higher alcohol (lauryl alcohol, isopropanol, isostearyl alcohol, octyldodecanol, oleyl alcohol, etc.), a fatty acid (isostearic acid, lauric acid, adipic acid, sebacic acid, myristic acid, etc.), a dibasic acid diester (diethyl sebacate, diisopropyl sebacate, diisopropyl adipate, etc.), triacetin, benzyl alcohol, cetyl lactate, octyldodecyl lactate, liquid paraffin, and a mixture of two or more kinds thereof.

Examples of the softener may include paraffin oil such as liquid paraffin, animal oil such as squalane and squalene, vegetable oil such as almond oil, olive oil, camellia oil, castor oil, tall oil, and peanut oil, silicone oil, polybutene, middle-chain fatty acid triglyceride, glycerol monostearate, isopropyl myristate, diisopropyl adipate, dipropylene glycol, and a mixture of two or more kinds thereof.

Examples of the absorption enhancer may include triacetin, fatty acid or aliphatic alcohol (lauric acid, myristic acid, oleyl alcohol, isopropanol, lauryl alcohol, dipropylene glycol, propylene glycol, etc.), a fatty acid ester (glyceryl monolaurate, glyceryl monooleate, cetyl lactate, octyldodecyl lactate, glycerol monolaurate, glycerol monooleate, propylene glycol monolaurate, propylene glycol monooleate, sorbitane monolaurate, sorbitane monooleate, etc.), and a mixture of two or more kinds thereof.

Examples of the skin irritation alleviating agent may include glycerol, allantoin, antihistaminic agent (diphenhydramine, etc.), an antiphlogistic (glycyrrhetinic acid, etc.), a steroid agent, and a mixture of two or more kinds thereof.

Examples of the antioxidant may include dibutylhydroxytoluene (BHT), DL-$\alpha$-tocopherol, ascorbic acid palmitate, and a mixture of two or more kinds thereof.

Further, other components may also be contained as the additive. Specific examples thereof may include a petroleum resin (Quinton, ARKON, etc.); a surfactant (polyoxyethylene hydrogenated castor oil 20, polyoxyethylene hydrogenated castor oil 60, a polyoxyethylene sorbitol fatty acid ester (polysorbate 20, polysorbate 60, polysorbate 80, polyoxyethylene sorbitan monolaurate, etc.), a polyoxyethylene fatty acid ester (polyoxyl stearate 40, etc.), a sorbitan fatty acid ester (sorbitan monooleate, sorbitan trioleate, sorbitan monolaurate, sorbitan sesquioleate, etc.), self-emulsification-type glycerol monostearate, glycerol monostearate, sorbitan monostearate, a sucrose fatty acid ester, macrogol 400, lauromacrogol, polyoxyethylene lauryl ether sodium phosphate, polyoxyethylene oleyl ether phosphate, polyoxyethylene nonyl phenyl ether, polyoxyethylene octyl phenyl ether, polyoxyethylene polyoxypropylene glycol (polyoxyethylene (120) polyoxypropylene (40) glycol, polyoxyethylene (160) polyoxypropylene (30) glycol, polyoxyethylene (20) polyoxypropylene (20) glycol, etc.), polyoxyethylene polyoxypropylene decyl tetradecyl ether, alkyl allyl polyether alcohol, polyoxyethylene cetyl ether, polyoxyethylene oleylamine, polyoxyethylene sorbitol beeswax, diethanolamide laurate, stearyl alcohol, a dibasic acid diester (diethyl sebacate, etc.), squalane, cetanol, cetomacrogol 1000, etc.); a flavoring agent (peppermint oil, orange oil, chamomile oil, spearmint oil, clove oil, turpentine oil, pine oil, himalayan cedar oil, bergamot oil, eucalyptus oil, lavender oil, rose oil, roman chamomile oil, Perubalsam, d-camphor, dl-camphor, d-borneol, dl-borneol, dl-menthol, 1-menthol, geraniol, methyl salicylate, cinnamaldehyde, piperonal, etc.), and a mixture of two or more kinds thereof.

The transdermal absorption preparation of this embodiment can be produced by forming a rubber-based adhesive layer on a support. It is preferable that the adhesive layer be coated with a release liner until use in order to protect the adhesive layer. A method for producing the transdermal absorption preparation of this embodiment is not particularly limited, and can be appropriately selected by those skilled in the art.

For example, the transdermal absorption preparation of this embodiment can be produced by a method that is generally referred to as a hot melt method or a method that is referred to as a solvent method.

According to the hot melt method, for example, a mixture (base component) of imidafenacin, an additive, and a rubber-based additive is thermally molten, and then applied to a release film or a support to form an adhesive layer. Subsequently, the adhesive layer formed is bonded to a support or a release film to obtain a transdermal absorption preparation.

According to the solvent method, for example, a mixture of imidafenacin, an additive, and a rubber-based adhesive is dissolved in an organic solvent such as methanol, ethanol, ethyl acetate, chloroform, or hexane, and then spread on or applied to a release film or a support. The solvent is then removed by drying to form an adhesive layer. Subsequently, the adhesive layer formed is bonded to a support or a release film to obtain a transdermal absorption preparation.

The size or thickness of the adhesive layer is not particularly limited and can be appropriately determined by those skilled in the art.

A material for the support of the transdermal absorption preparation of this embodiment is not particularly limited, and can be appropriately selected by those skilled in the art. For example, a stretchable or non-stretchable support may be used. For example, it is selected from a fabric, a non-woven fabric, polyurethane, polyester, polyvinyl acetate, polyvinylidene chloride, polyethylene, polyethylene terephthalate (PET), an aluminum sheet, and a composite material thereof.

A material for the release film is not particularly limited and can be appropriately selected by those skilled in the art. Specific examples thereof may include a polyethylene film, a PET film, and a polypropylene film that are coated with silicon.

Imidafenacin has a selective antagonism of muscarine receptors M3 and M1 in smooth muscles of the bladder, the trachea, the gastrointestinal tracts, and the like. Therefore, the transdermal absorption preparation of this embodiment is useful as a preventive drug and/or a therapeutic drug for pollakiuria and urinary incontinence accompanying overactive bladder (OAB), asthma, chronic obstructive pulmonary disease (COPD), irritable bowel syndrome (IBS), or the like.

A method of administering imidafenacin using the transdermal absorption preparation of this embodiment is appropriately determined based on a disease to be prevented or treated, or a state of a patient to be administered. For example, the method may be an administration form of applying the preparation twice a day or once a day. Alternatively, the method may be an administration form of applying the preparation before going to bed or before a necessary situation.

An applied region is not particularly limited, and for example, it is the back of the ear, the arms, the abdomen such as the lower abdomen, the chest, the back, the waist, the hip, or the legs such as the inside of the thighs and the calves.

In this embodiment, the amount of imidafenacin included in the adhesive layer is not particularly limited, and is determined based on a disease to be prevented or treated, the size of the adhesive layer, an administration time, the blood level of imidafenacin to be targeted, or the like. For example, the amount of imidafenacin to be contained in one preparation or one time administration preparation may be about 0.1 mg to about 30 mg.

When the rubber-based adhesive layer of the transdermal absorption preparation of this embodiment contains oleic acid, capric acid, and crotamiton together with imidafenacin, the transdermal absorbability of imidafenacin can be enhanced. When the adhesive layer contains a carboxylic acid having 2 to 10 carbon atoms, the transdermal absorbability of imidafenacin can be further enhanced. When the adhesive layer contains a fatty acid ester having 6 to 20 carbon atoms, the transdermal absorbability of imidafenacin can be more enhanced.

In this manner, the transdermal absorbability of imidafenacin can be enhanced. Therefore, according to the transdermal absorption preparation of this embodiment, for example, imidafenacin can be effectively absorbed in the circulating blood through the skin. A side effect that may be caused by a rapid increase of the blood level in oral administration can also be avoided. Accordingly, the transdermal absorption preparation of this embodiment is very useful as preventive and/or therapeutic agents for pollakiuria and urinary incontinence accompanying overactive bladder (OAB), asthma, COPD, IBS, and the like.

EXAMPLES

Hereinafter, the present invention will be described in detail. However, the transdermal absorption preparation of the present invention is not limited to embodiments described in Examples.

Example 1

37.5 g of chloroform was added to 0.5 g of 4-(2-methyl-1-imidazolyl)-2,2-diphenylbutylamide weighted in advance, and stirred for dissolution to obtain an imidafenacin solution. In the obtained imidafenacin solution, 3.71 g of styrene-isoprene-styrene block copolymer, 4.0 g of hydrogenated rosin glycerol ester, 1.0 g of isopropyl myristate, 0.5 g of oleic acid, 0.09 g of capric acid, 0.1 g of crotamiton, and 0.1 g of lactic acid were dissolved while stirring to prepare an adhesive layer liquid. The adhesive layer liquid was spread over a polyester face of Scotchpak#9742 that was a support with a baker-type applicator of which the thickness scale was set to 10. The Scotchpak#5742 on which the adhesive layer liquid was spread was dried at room temperature for 15 minutes, and then dried in ISUZU BEST DRYING of which the drying temperature was set to 60° C. for about 15 minutes, to form an adhesive layer. A face (adhesive surface) of the formed adhesive layer to come into contact with the skin during use was coated with a fluorine polymer face of Scotchpak#9742 to form a transdermal absorption preparation.

Example 2 and Comparative Examples 1 to 14

Transdermal absorption preparations in Example 2 and Comparative Examples 1 to 14 were prepared in the same manner as in Example 1 except that the ratios of components to be contained were changed. The amounts of the components contained in each of the adhesive layers in Examples and Comparative Examples are shown in FIG. 1.

[Method for In Vitro Rat Skin Permeability Test]

The abdomen skin of a hairless rat was cut under ether anesthesia, fat on the dermis side was removed, and the abdomen skin was mounted on a lateral diffusion cell (effective diffusion area: 0.95 $cm^2$, cell volume: 3 mL). The transdermal absorption preparation of each of Examples and Comparative Examples was then stuck to the skin mounted on the cell on the stratum corneum side. A 0.01 M phosphate buffer solution (pH 7.4, containing 0.85% sodium chloride, hereinafter also referred to as receptor liquid) was injected in the cell positioned at the dermis side of the skin. A part (500 μL) of receptor liquid was sampled with time. At each time, the cell was charged with 500 μL of 0.01 M phosphate buffer solution (pH 7.4, containing 0.85% sodium chloride). The concentration of imidafenacin in the sampled receptor liquid was measured under the following measurement conditions through a high performance liquid chromatography (HPLC) method.

(HPLC Conditions)

Injection volume; 20 μL

Detector: UV absorption spectrophotometer (measurement wavelength: 220 nm)

Column: Inertsil ODS-2, 4.6 mm×15 cm, 5 μm, manufactured by GL Sciences Inc.

Column temperature: 30° C.

Mobile phase: solution of 0.005 M sodium 1-octane sulfonate solution in diluted phosphoric acid (1→100):acetonitrile (7:3)

Flow rate: about 1.0 mL/min (retention time of imidafenacin: about 7 min)

From the results of the measurements, the cumulative drug permeability amount per square centimeter (μg/$cm^2$) of the preparation at each sampling point was calculated, and a relationship between the time and the cumulative drug permeability amount was plotted. After that, the correlation line of the cumulative permeability amount was calculated from the graph, and the inclination thereof was regarded as a FLUX value that was a drug permeability rate. (FLUX: amount of drug transdermally absorbed from 1 $cm^2$ of the preparation per hour after applying)

The resulting FLUX values are shown in FIG. 2.

The FLUX value in Example 1 was 6.3 μg/$cm^2$/hour, and the FLUX value in Example 2 was 5.3 μg/$cm^2$/hour. Sven the highest FLUX value in Comparative Examples was mere 4.3 μg/$cm^2$/hour (Comparative Example 9).

The transdermal absorption preparations in Examples 1 to 2 exhibited high transdermal absorbability of imidafenacin as compared with the transdermal absorption preparations in Comparative Examples. In the transdermal absorption preparation in Example 1 that contained lactic acid in addition to oleic acid, capric acid, and crotamiton, the higher transdermal absorbability than any other Examples was confirmed.

INDUSTRIAL APPLICABILITY

The transdermal absorption preparation of the present invention is useful as prevention and/or treatment for pollakiuria and urinary incontinence accompanying overactive bladder (OAB), asthma, chronic obstructive pulmonary disease (COPD), irritable bowel syndrome (IBS), and the like.

The invention claimed is:

1. A transdermal absorption preparation comprising:

(1) a support, and (2) a rubber-based adhesive layer comprising 4-(2-methyl-1-imidazolyl)-2,2-diphenylbutylamide or a pharmaceutically acceptable salt thereof, oleic acid, capric acid and crotamiton, wherein the rubber-based adhesive layer is formed on a surface of the support, and wherein the transdermal absorption preparation has a FLUX value of at least 5.3 $\mu g/cm^2/hour$.

2. The transdermal absorption preparation according to claim 1, wherein the rubber-based adhesive layer further comprises a carboxylic acid having 2 to 10 carbon atoms.

3. The transdermal absorption preparation according to claim 2, wherein the carboxylic acid having 2 to 10 carbon atoms is lactic acid.

4. The transdermal absorption preparation according to claim 1, wherein the rubber-based adhesive layer further comprises a fatty acid ester having 6 to 20 carbon atoms.

5. The transdermal absorption preparation according to claim 4, wherein the fatty acid ester having 6 to 20 carbon atoms is isopropyl myristate.

6. The transdermal absorption preparation according to claim 2, wherein the rubber-based adhesive layer further comprises a fatty acid ester having 6 to 20 carbon atoms.

7. The transdermal absorption preparation according to claim 3, wherein the rubber-based adhesive layer further comprises a fatty acid ester having 6 to 20 carbon atoms.

8. The transdermal absorption preparation according to claim 6, wherein the fatty acid ester having 6 to 20 carbon atoms is isopropyl myristate.

9. The transdermal absorption preparation according to claim 7, wherein the fatty acid ester having 6 to 20 carbon atoms is isopropyl myristate.

* * * * *